United States Patent
Slater et al.

(10) Patent No.: US 11,490,843 B2
(45) Date of Patent: Nov. 8, 2022

(54) VEHICLE OCCUPANT HEALTH MONITOR SYSTEM AND METHOD

(71) Applicant: TOYOTA MOTOR NORTH AMERICA, INC., Plano, TX (US)

(72) Inventors: Robert D. Slater, Murphy, TX (US); Mathew D. Gardner, Lewisville, TX (US); Shingo Sugimoto, Frisco, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 870 days.

(21) Appl. No.: 16/193,512

(22) Filed: Nov. 16, 2018

(65) Prior Publication Data

US 2020/0155054 A1 May 21, 2020

(51) Int. Cl.
| | | |
|---|---|---|
| A61B 5/00 | (2006.01) | |
| A61B 5/18 | (2006.01) | |
| A61B 5/024 | (2006.01) | |
| A61B 5/021 | (2006.01) | |
| A61B 5/01 | (2006.01) | |
| A61B 5/08 | (2006.01) | |
| A61B 5/16 | (2006.01) | |
| G06V 20/59 | (2022.01) | |
| B60H 1/00 | (2006.01) | |

(52) U.S. Cl.
CPC .............. *A61B 5/18* (2013.01); *A61B 5/01* (2013.01); *A61B 5/021* (2013.01); *A61B 5/02416* (2013.01); *A61B 5/08* (2013.01); *A61B 5/165* (2013.01); *A61B 5/6893* (2013.01); *A61B 5/7282* (2013.01); *A61B 5/7435* (2013.01); *A61B 5/7475* (2013.01); *G06V 20/597* (2022.01); *A61B 5/0077* (2013.01); *B60H 1/00742* (2013.01); *B60H 1/00792* (2013.01)

(58) Field of Classification Search
None
See application file for complete search history.

(56) References Cited

U.S. PATENT DOCUMENTS

| | | | |
|---|---|---|---|
| 6,724,920 B1 | 4/2004 | Berenz et al. | |
| 8,576,081 B2 | 11/2013 | Hatakeyama et al. | |
| 9,124,955 B2 | 9/2015 | Geva et al. | |
| 9,932,041 B2 | 4/2018 | Kim et al. | |
| 10,040,423 B2 | 8/2018 | Boesen | |
| 2005/0043864 A1* | 2/2005 | Echtenkamp | B60R 16/0231 701/1 |
| 2007/0257804 A1* | 11/2007 | Gunderson | G06Q 40/08 340/576 |
| 2013/0070043 A1* | 3/2013 | Geva | B60K 28/066 348/14.02 |

(Continued)

FOREIGN PATENT DOCUMENTS

| | | |
|---|---|---|
| CA | 2900168 A1 | 8/2015 |
| CN | 102211522 A | 10/2011 |
| KR | 101839055 B1 | 3/2018 |

*Primary Examiner* — Yi-Shan Yang
(74) *Attorney, Agent, or Firm* — Haynes and Boone, LLP (57) ABSTRACT

Apparatus, systems, and methods for methods for monitoring the health status of a vehicle occupant by detecting when a triggering physiological condition is met, confirming the triggering physiological condition is real by identifying a separate vehicle triggering event, and automatically responding to minimize the potential impact of the triggering event.

20 Claims, 5 Drawing Sheets

(56) References Cited

U.S. PATENT DOCUMENTS

| | | | |
|---|---|---|---|
| 2014/0275834 A1* | 9/2014 | Bennett | A61B 5/6893 |
| | | | 600/301 |
| 2014/0379273 A1* | 12/2014 | Petisce | G16H 40/67 |
| | | | 702/19 |
| 2015/0057557 A1* | 2/2015 | Howie | A61B 5/316 |
| | | | 600/509 |
| 2016/0086491 A1 | 3/2016 | Choi | |
| 2016/0150070 A1* | 5/2016 | Goren | G06K 9/00805 |
| | | | 455/404.2 |
| 2016/0207454 A1 | 7/2016 | Cuddihy et al. | |
| 2016/0354027 A1* | 12/2016 | Benson | A61B 5/1102 |
| 2017/0274906 A1 | 9/2017 | Hassan et al. | |
| 2019/0357834 A1* | 11/2019 | Aarts | G08B 21/06 |

\* cited by examiner

VEHICLE OCCUPANT HEALTH MONITOR SYSTEM AND METHOD

TECHNICAL FIELD

The present disclosure relates generally to systems and methods for monitoring the health of a vehicle occupant and responding during a health-related situation.

BACKGROUND

Many car accidents occur due to unforeseen medical conditions of the drivers. For example, a driver may experience a sudden heart attack, a seizure, a stroke, a loss of consciousness or some other condition that results in the driver losing awareness or attentiveness that may result in a loss of vehicle control, potentially causing an accident.

Some vehicles include driver drowsiness monitoring systems that detect when the driver is becoming drowsy. These systems alert the driver to pull over or may take other action. This type of a system may be used to proactively identify when a driver is experiencing an unsafe condition, such as a medical condition. As these systems become more complex, it becomes more important to verify the accuracy of these diagnostics to ensure that the response is appropriate to the medical condition.

SUMMARY

The present disclosure provides systems and methods for monitoring the health status of a vehicle occupant by detecting when a triggering physiological condition is met, confirming the triggering physiological condition is real by identifying a separate vehicle triggering event, and automatically responding to minimize the potential impact of the triggering event.

In an exemplary aspect, the present disclosure is directed to a vehicle occupant health monitor system that may include an input device arranged to receive inputs from a vehicle occupant indicating a triggering event, a triggering physiological condition, and a preestablished action. The system may also include a health profile module comprising a custom health profile for a specific vehicle occupant defining a parameter of the triggering physiological condition. A sensor may be arranged to monitor an actual physiological condition of the vehicle occupant for the triggering physiological condition.

A diagnosis module may be configured to compare the actual physiological condition of the vehicle occupant to the health profile to detect a presence of the triggering physiological condition. The system may also include a vehicle control module arranged to perform the preestablished action when both a) the diagnosis module detects the presence of the triggering physiological condition and b) the triggering event occurs.

In some aspects, the custom health profile comprises at least one of an expected heart rate range, an expected posture range, an accepted pulse range, an accepted blood pressure range, an accepted stress level range, an expected body temperature range, and an expected respiration range. In some aspects, the system may include a user interface configured to receive an input from the vehicle occupant regarding the vehicle occupant's physiological condition, and configured to update the custom health profile based on the received input. In some aspects, the user interface is configured to query the vehicle occupant regarding the vehicle occupants physiological condition. In some aspects, the system may include an action module comprising the preestablished action, the preestablished action being based upon an input from the vehicle occupant. In some aspects, the system may include a user interface configured to receive an input from the vehicle, the user interface being configured to present a plurality of potential preestablished actions to the vehicle occupant, and configured to receive via the user interface a selected preestablished action. In some aspects, the system may include an event module comprising the triggering event, the triggering event being based upon an input from the vehicle occupant. In some aspects, the user interface is configured to present via the user interface a plurality of potential triggering events to the vehicle occupant, and configured to receive via the user interface a selected triggering event. In some aspects, the system may include an event module comprising a plurality of triggering events, the triggering events comprising at least one of hazard lights being activated, detected erratic driving, and idling beyond a set period of time. In some aspects, the sensor is a micro gesture detecting camera configured to detect one of a vehicle occupant's pulse, blood pressure, stress level, body temperature, or respiration. In some aspects, the custom health profile defines a parameter of the triggering physiological condition by defining an expected physiological condition.

In an exemplary aspect, the present disclosure is directed to a vehicle occupant health monitor system that may include a sensor arranged within the vehicle to monitor a sensed physiological condition of the vehicle occupant while in the vehicle, a control unit comprising a profile module comprising a health profile for the vehicle occupant comprising at least one expected physiological condition, and a diagnosis module of the control unit configured to compare the sensed physiological condition of the vehicle occupant to the expected physiological condition of the health profile and identify a presence of a triggering physiological condition. The profile module of the control unit may be configured to update the health profile based on the sensed physiological condition. The system may also include a health monitoring system arranged to receive an input from the vehicle occupant indicating a triggering event and a preestablished action. A vehicle control module may be arranged to perform the preestablished action after the profile module updates the health profile and when both a) the diagnosis module detects the presence of the triggering physiological condition and b) the triggering event occurs.

In some aspects, the system may include a user interface configured to receive information from the vehicle occupant regarding the vehicle occupant's current physiological condition, and wherein the profile module of the control unit is configured to update the health profile based on the information from the vehicle occupant regarding the vehicle occupant's current physiological condition. In some aspects, the user interface is configured to query the vehicle occupant regarding the vehicle occupants physiological condition. In some aspects, the sensor is a micro gesture detecting camera configured to detect one of a vehicle occupant's pulse, blood pressure, stress level, body temperature, or respiration. In some aspects, the health profile comprises at least one of an expected heart rate range, an expected posture range, an accepted pulse range, an accepted blood pressure range, an expected stress level range, an expected body temperature range, and an expected respiration range.

In an exemplary aspect, the present disclosure is directed to a method of monitoring and responding to a vehicle occupant's health. The method may include generating a custom health profile for a specific vehicle occupant comprising at least one expected physiological condition; receiving an input at an input device from a vehicle occupant indicating a triggering event and a preestablished action; monitoring with a sensor an actual physiological condition of the vehicle occupant; comparing with a diagnosis module the actual physiological condition of the vehicle occupant to the expected physiological condition; and performing with a vehicle control module the preestablished action when both a) the diagnosis module detects the presence of the triggering physiological condition and b) the triggering event occurs.

In some aspects, monitoring with a sensor comprises monitoring with a micro gesture detecting camera configured to detect one of the vehicle occupants pulse, blood pressure, stress level, body temperature, or respiration. In some aspects, the method may include receiving at an input device information from the vehicle occupant regarding the vehicle occupant's current physiological condition, and updating the health profile based on the information from the vehicle occupant regarding the vehicle occupant's current physiological condition. In some aspects, the method may include querying the vehicle occupant regarding the vehicle occupants physiological condition.

DETAILED DESCRIPTION

The illustrative implementations and related methods of the present disclosure are described below as they might be employed in a system and method for vehicle occupant health monitoring. In the interest of clarity, not all features of an actual implementation or method are described in this specification. It will of course be appreciated that in the development of any such actual implementation, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various implementations and related methods of the disclosure will become apparent from consideration of the following description and drawings.

The present disclosure is directed to vehicle occupant health monitoring systems and methods that monitor health metrics of a vehicle occupant, such as a driver, monitors in-vehicle conditions or events, and takes action in response to the health metrics and the conditions or events to help mitigate the effects of an emergency health condition. In some implementations, the systems and methods described herein may be customized by a vehicle occupant based on a health profile built over time, based on desired vehicle triggering events, and based on preestablished responsive actions. For example, a vehicle may have a health monitoring engine that includes a custom health profile for a specific vehicle occupant. A health sensor engine may monitor the physiological condition of the vehicle occupant, and may update the custom health profile for the specific vehicle occupant based on the monitored physiological condition. Over time, this custom health profile may become more sensitive and accurate as a baseline physiological condition of the vehicle occupant.

When the vehicle occupant health monitoring system detects that the physiological condition of the vehicle occupant is outside of the expected health profile (e.g., a triggering physiological event), the system may act to assist the vehicle occupant to mitigate the effects of a potential health situation, such as a crisis. In some implementations, in addition to a triggering physiological condition, vehicle sensors detect whether a triggering event is also satisfied to confirm that a health situation is indeed occurring. This may reduce the likelihood of the vehicle taking an automatic remedial response when it is neither necessary nor desired. Finally, the vehicle may take the automatic remedial action when the sensed triggering physiological condition is outside the custom profile and the triggering event has occurred. Both the triggering event and the automatic remedial action may be individually pre-selected by the vehicle occupant, thereby giving the vehicle occupant additional control.

Figure 1:
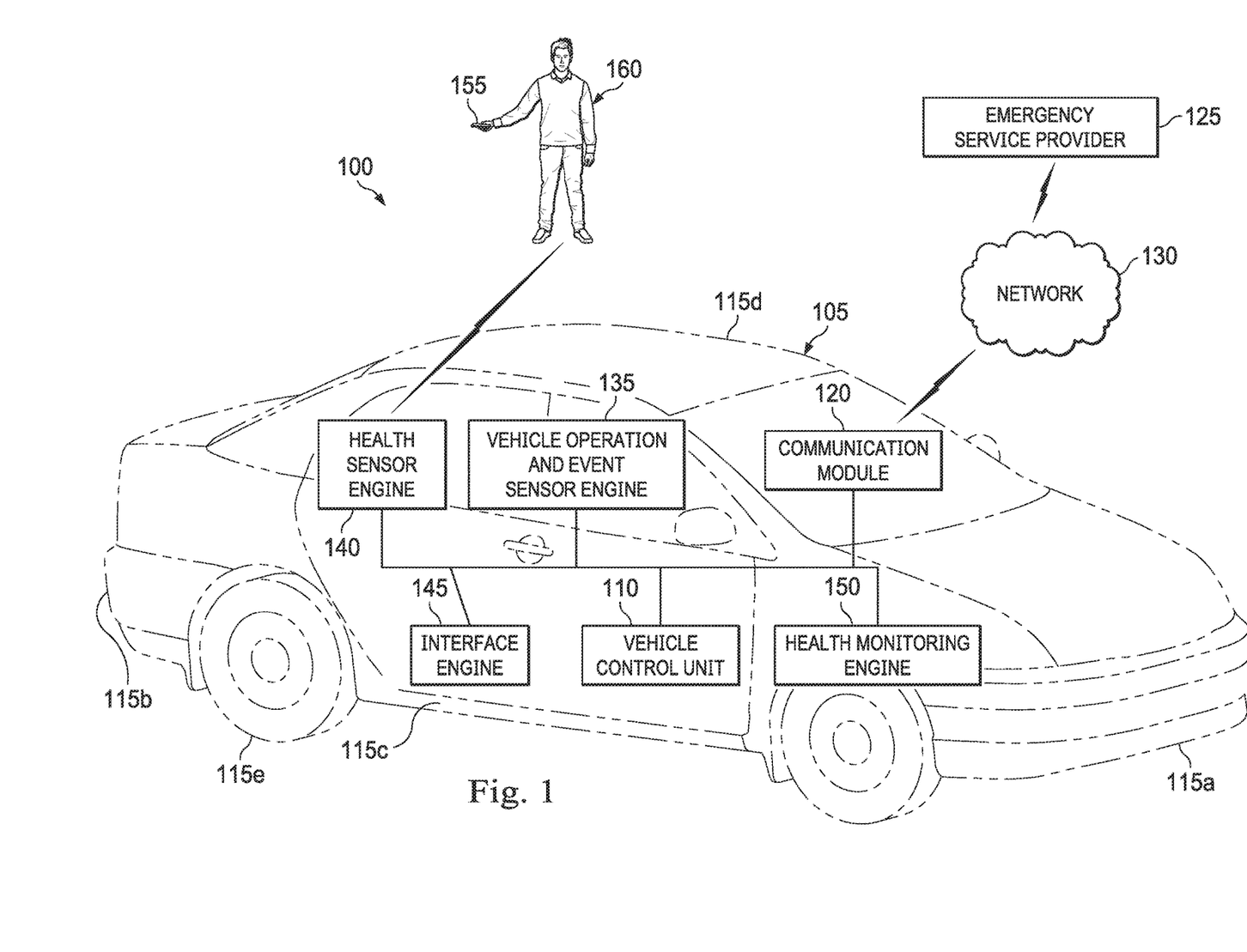
FIG. 1 is a diagrammatic illustration of a vehicle occupant health monitoring system according to one or more implementations of the present disclosure.

FIG. 1 illustrates an exemplary vehicle occupant health monitoring system 100. As described herein, the vehicle occupant health monitoring system 100 is arranged to monitor the health or physiological condition of a vehicle occupant for a triggering physiological condition, monitor an internal or external condition of the vehicle for a triggering event, and automatically take a remedial action if both the triggering physiological condition of the vehicle occupant and the triggering event of the vehicle is met.

The health monitoring system 100 includes a vehicle 105, such as an automobile, and a vehicle control unit 110 located on the vehicle 105. The vehicle 105 may include a front portion 115a (including a front bumper), a rear portion 115b (including a rear bumper), a right-side portion 115c (including a right front quarter panel, a right front door, a right rear door, and a right rear quarter panel), a left side portion 115d (including a left front quarter panel, a left front door, a left rear door, and a left rear quarter panel), and wheels 115e. A communication module 120 is operably coupled to, and adapted to be in communication with, the vehicle control unit 110. The communication module 120 is adapted to communicate wirelessly with an emergency service provider 125 via a network 130 (e.g., a 3G network, a 4G network, a 5G network, a Wi-Fi network, an ad hoc network, or the like). The network 130 may include one or more off-vehicle servers or processors that perform processing functions for any of the components of the vehicle 105.

A vehicle operation and event sensor engine 135 is operably coupled to, and adapted to be in communication with, the vehicle control unit 110. The vehicle operation and event sensor engine 135 is adapted to monitor various components and parameters of the vehicle, for example, the engine, speed, and direction, among others, and/or the surrounding environment, for example, temperature, weather, road conditions, among others, as described in further detail below. A health sensor engine 140 is operably coupled to, or adapted to be in communication with, the vehicle control unit 110. The health sensor engine 140 is configured to monitor the physiological status of a vehicle occupant. It may do this using any of a variety of sensors disposed about the vehicle 105, as well as using any of a variety of personal sensors 155 carried by or worn by a vehicle occupant 160. An interface engine 145 is operably coupled to, and adapted to be in communication with, the vehicle control unit 110. The interface engine 145 may be configured to output information or data to a vehicle occupant, such as a driver, and receive inputs or information from the vehicle occupant. A health monitoring engine 150 is operably coupled to, and adapted to be in communication with the vehicle control unit 110. In addition to, or instead of, being operably coupled to, and adapted to be in communication with, the vehicle control unit 110, the communication module 120, the operation and event sensor engine 135, the health sensor engine 140, the interface engine 145, and/or the health monitoring engine 150 may be operably coupled to, and adapted to be in communication with, one another via wired or wireless communication (e.g., via an in-vehicle network). In some implementations, as in FIG. 1, the vehicle control unit 110 is adapted to communicate with the communication module 120, the vehicle operation and event sensor engine 135, the health sensor engine 140, the interface engine 145, and the health monitoring engine 150 to at least partially control the interaction of data with and between the various components of the vehicle occupant health monitoring system 100.

The term "engine" is meant herein to refer to an agent, instrument, or combination of either, or both, agents and instruments that may be associated to serve a purpose or accomplish a task—agents and instruments may include sensors, actuators, switches, relays, power plants, system wiring, computers, components of computers, programmable logic devices, microprocessors, software, software routines, software modules, communication equipment, networks, network services, and/or other elements and their equivalents that contribute to the purpose or task to be accomplished by the engine. Accordingly, some of the engines may be software modules or routines, while others of the engines may be hardware and/or equipment elements in communication with the vehicle control unit 110, the communication module 120, the network 130 and any associated server, and/or the emergency service provider 125.

The emergency service provider 125 may be a public or private organization providing emergency response services. For example, the emergency service provider 125 may be first responders such as police, fire, or ambulance responders or other emergency service provider.

Figure 2:
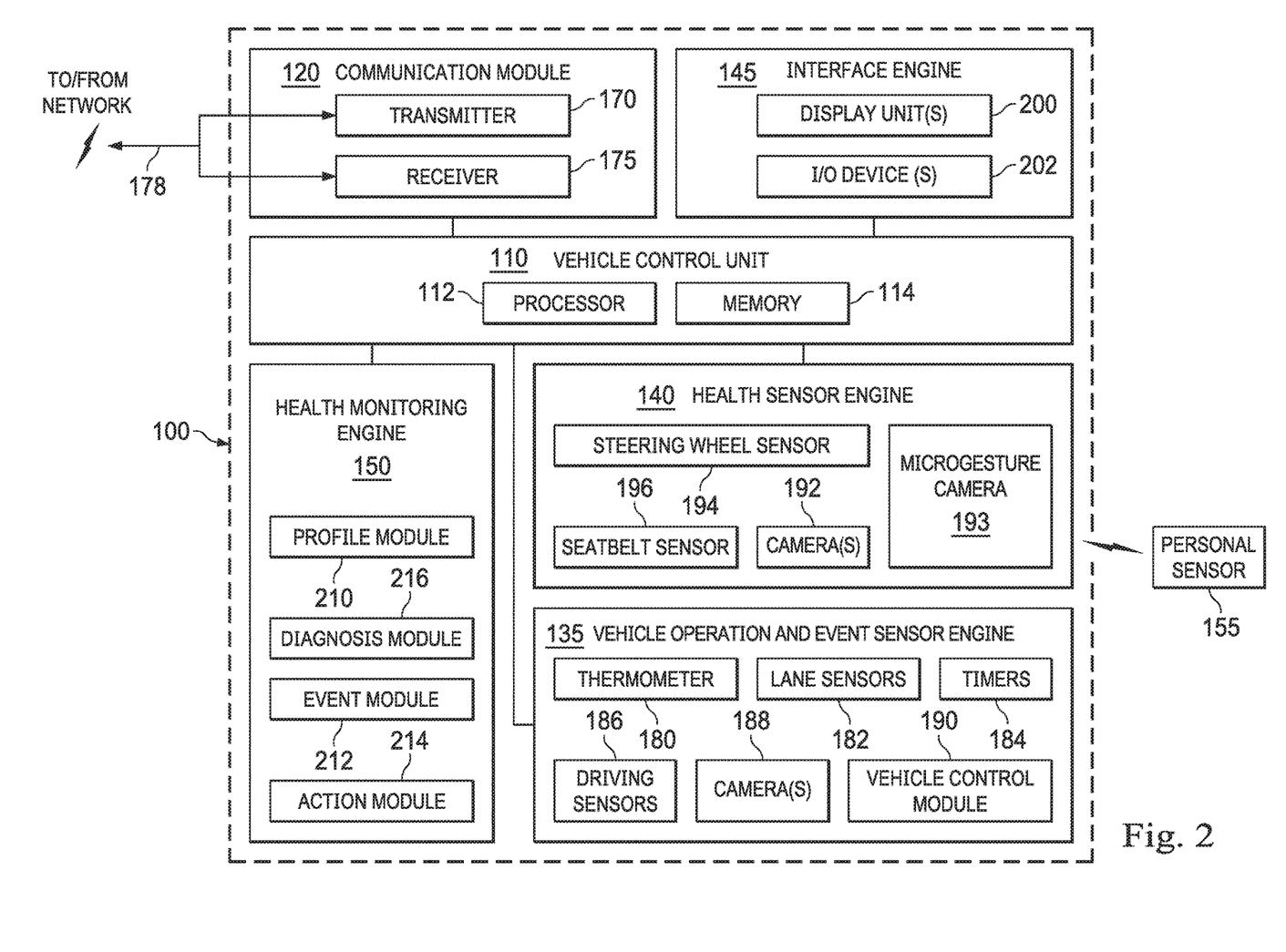
FIG. 2 is a block diagrammatic illustration of the vehicle occupant health monitoring system according to one or more implementations of the present disclosure.

Referring to FIG. 2, a detailed diagrammatic view of the system 100 of FIG. 1 is illustrated. With reference to FIG. 2, the vehicle control unit 110 includes a processor 112 and a memory 114. In some implementations, the vehicle control unit 110 processes information from the communication module 120, the vehicle operation and event sensor engine 135, the health sensor engine 140, the interface engine 145, and the health monitoring engine 150. In other implementations, each of the modules and engines includes their own processor and memory that cooperate with the processors and memory of each of the other modules and engines. Accordingly, in some implementations, the vehicle control unit 110 forms a part of any one or more of the described modules or engines.

In some implementations, as in FIG. 2, the communication module 120, which is operably coupled to and adapted to be in communication with the vehicle control unit 110, includes a transmitter 170 and a receiver 175. In some implementations, one or the other of the transmitter 170 and the receiver 175 may be omitted according to the particular application for which the communication module 120 is to be used. In some implementations, the transmitter 170 and the receiver 175 are combined into a transceiver capable of both sending and receiving wireless signals. In any case, the transmitter 170 and the receiver 175 are adapted to send/receive data to/from the network 130, as indicated by arrow 178.

In some implementations, as in FIG. 2, the vehicle operation and event sensor engine 135, which is operably coupled to, and adapted to be in communication with, the vehicle control unit 110, includes a plurality of devices configured to facilitate driving of the vehicle 105, monitoring of the vehicle and vehicle components, and monitoring the internal and external environment of the vehicle 105. In this regard, the vehicle operation and event sensor engine 135 may be designed to exchange communication with the vehicle control unit 110, to not only receive instructions, but to provide information on the operation of the vehicle 105. For example, the vehicle operation and event sensor engine 135 may include vehicle components including, for example, a vehicle battery, a motor (e.g., electric or combustion), a drivetrain, a steering system, and a braking system. The vehicle battery provides electrical power to the motor, which motor drives the wheels 115e of the vehicle 105 via the drivetrain. The vehicle operation and event sensor engine 135 may also include one or more sensors for monitoring any of the vehicle components, driving behavior, environmental conditions, or other factors that may be used to determine when a health situation is underway. In the implementation shown in FIG. 2, the vehicle operation and event sensor engine includes a thermometer 180, drive assist sensors shown here as lane sensors 182, timers 184, driving sensors 186 which may include proximity sensors, sonar, radar, or other sensors that may assist with driving, cameras 188 associated with image recognition technology, and other vehicle sensors disposed about the vehicle 105, including sensors associated with and monitoring vehicle components such as the battery, the motor, the drivetrain, the steering system, and the braking system. The vehicle operation and event sensor engine 135 may include a speedometer, a tachometer, an accelerometer, a global positioning system (GPS), vehicle camera(s), vehicle microphone(s), vehicle impact sensor(s), an airbag sensor, a braking sensor, and other sensors or any combination thereof. The sensors or other detection devices are generally configured to sense or detect activity, conditions, and circumstances in an area to which the device has access. As will be described herein, the vehicle operation and event sensor engine 135 may be configured to identify the occurrence of a triggering event relating to the vehicle 105 and/or the condition or environment of the vehicle. As described herein, a triggering event may be initiated, in cooperation with a health-related event, such as a physiological triggering event, to initiate an automatic response by the vehicle 105.

The vehicle operation and event sensor engine 135 may also include a vehicle control module 190. The vehicle control module 190 may be configured to automatically respond to a triggering physiological condition and a triggering vehicle event to mitigate the consequences of the health situation. For example, the vehicle control module 190 may be configured to operate the vehicle 105 when the vehicle occupant health monitoring system 100 determines that the driver of the vehicle 105 is not in condition for safe operation of the vehicle 105. As will be described below, the vehicle control module 190 may include many of the same or similar elements described above, including a GPS, cameras, microphones, sensors, and other vehicle control elements such as climate control, seat temperature controls, vehicle autopilot, communication elements, hazard light control, and other elements.

In some implementations, as in FIG. 2, the health sensor engine 140, which is operably coupled to, and adapted to be in communication with, the vehicle control unit 110, includes devices such as sensors, detectors, or other devices configured to measure or sense a parameter related to a physiological condition of the vehicle occupant, such as the driver of the vehicle 105. The health sensor engine may include for example camera(s) 192, a micro gesture camera 193, a steering wheel sensor 194, a seatbelt sensor 196, and other sensors or detectors capable of identifying a physiological condition of the vehicle occupant. The cameras 192 may be positioned to monitor any physical indication of the vehicle occupant's physiological status. In some implementations, the cameras 192 may be configured to capture a vehicle occupants posture, pupil dilation, and eyelid condition such as whether the eyelids are closing, for example. The micro gesture camera 193 may be configured to identify micro-gestures not visible to the human eye. For example, the micro gesture camera 193 may be configured to identify pulse, blood pressure, stress levels, body temperature, respiration, or other micro-gestures not visible to a human eye.

The steering wheel sensor 194 may be able to monitor a vehicle occupant's physiological status by detecting grip strength, responsiveness to lane deviations, or other indicators of physiological status. The seatbelt sensor 196 may be configured to monitor a vehicle occupant's physiological status by detecting posture, heart rate, or other indicator of physiological status. Additional sensors or detectors may be included in the health sensor engine. The list provided includes only a few examples.

In some implementations, the personal sensor 155, which may be worn by the vehicle occupant 160 as shown in FIG. 1. The personal sensor 155 may be a sensor or indicator of the physiological status of the vehicle occupant 160. In some implementations, the personal sensor(s) 155 may be worn on a wrist, on a user's chest, or elsewhere about the body to detect physiological condition. Some examples include health monitoring watches, pulse detectors, blood pressure detectors, stress detectors, body temperature thermometers, or other personal sensor 155 that may be worn or carried about the vehicle occupant. In other examples, the personal sensor 155 is, includes, or is part of one or more computing devices such as personal computers, personal digital assistants, cellular devices, mobile telephones, wireless devices, handheld devices, laptops, audio devices, tablet computers, game consoles, cameras, and/or any other suitable devices. In the implementation shown, the personal sensor 155 communicates with the health sensor engine 140. Depending upon the implementation, the personal sensor 155 may communicate directly with the health sensor engine 140, or may communicate with the communication module 120 of the vehicle 105. In some implementations, the personal sensor 155 belonging to an occupant of the vehicle 105 may be coupled to, and adapted to be in communication with, the interface engine 145. For example, the personal sensor 155 may be coupled to, and adapted to be in communication with, the interface engine 145 via the I/O device 202 (e.g., the USB port and/or the Bluetooth communication interface). In an implementation, the personal sensor 155 is a handheld or otherwise portable device which is carried onto the vehicle 105 by a user who is a driver or a passenger on the vehicle 105. In several implementations, the personal sensor 1255 is a smartphone such as, for example, an iPhone® by Apple Inc. In some implementations, the personal sensor 155 may communicate information relating to the user's physiological status to the health sensor engine 140.

The interface engine 145, which is operably coupled to, and adapted to be in communication with, the vehicle control unit 110, includes at least one input and output device or system that enables a user to interact with the vehicle control unit 110 and the functions that the vehicle control unit 110 provides.

In the implementation shown, the interface engine 145 includes a display unit 200 and an input/output ("I/O") device 202. The display unit 200 may include any form of conveying information to a user. In some implementations, it may include a screen or other display that may show visual images such as text, illustrations, graphs, or other information relating to the vehicle occupant health monitoring system 100. The display unit 200 may be, include, or be part of multiple display units. For example, in some implementations, the display unit 200 may include one, or any combination, of a central display unit associated with a dash of the vehicle 105, an instrument cluster display unit associated with an instrument cluster of the vehicle 105, and/or a heads-up display unit associated with the dash and a windshield of the vehicle 105; accordingly, as used herein the reference numeral 200 may refer to one, or any combination, of the display units. The I/O device 202 may be, include, or be part of a communication port (e.g., a USB port), a Bluetooth communication interface, a touch-screen display unit, soft keys associated with a dash, a steering wheel, a keyboard, buttons, scroll wheels, knobs, dials, switches, voice-activated dialogue or other components enabling a vehicle occupant to input data or information into the vehicle occupant health monitoring system 100. Other examples of sub-components that may be part of the interface engine 145 include, but are not limited to, audible alarms, visual alerts, telecommunications equipment, and computer-related components, peripherals, and systems. In some implementations, the vehicle occupant may input data or information including custom programming relating to a user's health profile, triggering events indicative of a health situation, and custom responses regarding actions to be automatically taken by the vehicle 105 when the detected physiological condition of the vehicle occupant is outside of an acceptable range of physiological conditions and when a triggering event has occurred.

The health monitoring engine 150, which is operably coupled to, and adapted to be in communication with, the vehicle control unit 110, includes a plurality of modules such as a health profile module 210, an event module 212, and action module 214, and a diagnosis module 216.

The profile module 210 may include among other things, a vehicle occupant health profile. The vehicle occupant health profile may be customized to a particular individual that may be either a driver or a passenger of the vehicle 105.

In some implementations, the vehicle occupant health profile may be a dynamic profile regularly updated or reviewed by the vehicle control unit to ensure that the health profile is current and customized to a particular individual. In some examples, the health profile for a particular vehicle occupant may include expected physiological conditions for the vehicle occupant. The physiological conditions may include ranges of expected physiological parameters or measurements. Physiological parameters or measurements outside of the expected ranges may indicate a health situation (e.g., a triggering physiological event) and, when combined with a vehicle triggering event, may activate a response action to be taken by the vehicle 105.

Figure 3:
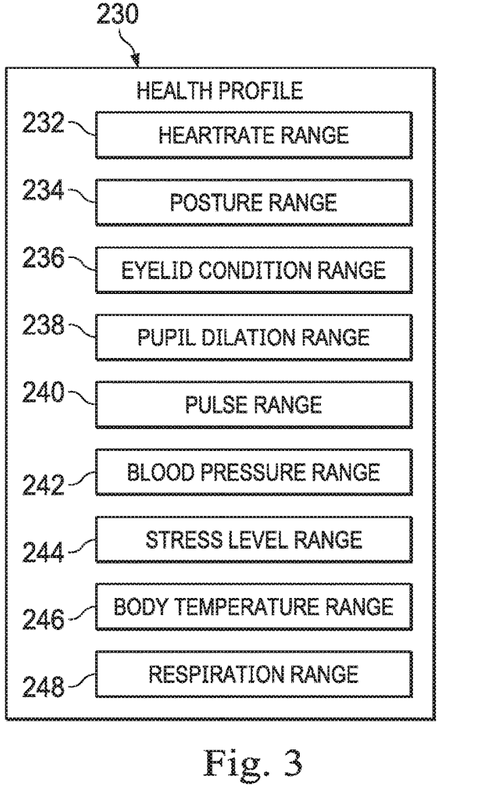
FIG. 3 is a block diagrammatic illustration of an example health profile forming a part of the vehicle occupant health monitoring system according to one or more implementations of the present disclosure.

FIG. 3 shows an example of a health profile 230 that may form a part of the profile module 210. In the implementation shown, the health profile 230 includes a plurality of physiological conditions that may be detected by the health sensor engine 140 and/or the personal sensor 155. In this implementation, the health profile 230 includes an acceptable range of physiological readings that may include, a heart rate range 232, a posture range 234, an eyelid condition range 236, a pupil dilation range 238, a pulse range 240, a blood pressure range 242, a stress level range 244, a body temperature range 246, a respiration range 248, among others. The acceptable physiological ranges of the health profile 230 define boundaries or parameters of the triggering physiological conditions. As indicated above, the health sensor engine 140 is configured to measure and detect any of the monitored physiological conditions identified in FIG. 3.

As indicated herein, the health profile 230 may be customized to a particular vehicle occupant. In some implementations, the health profile 230 is built over time based on sensed information captured by the health sensor engine 140 and the personal sensor 155. Accordingly, the vehicle control unit 110 may utilize the information captured at regular intervals or during continuous monitoring when the particular vehicle occupant is in the vehicle 105. In one example, the health sensor engine 140 may monitor a vehicle occupant's heart rate over time and establish a baseline acceptable heart rate range. For example, the heart rate may be monitored by the seatbelt sensor 196, the personal sensor 155. or may be monitored by micro gestures visible to the micro gesture camera 193 193. Over time, the health monitoring engine 150 may be configured to identify a heart rate range for the specific vehicle occupant that is indicative of a normal and customary heart rate for that vehicle occupant.

In some implementations, the health profile 230 may include an acceptable posture range 234. The vehicle occupant's posture may be monitored using the camera(s) 192, a seatbelt sensor 196, or other seat sensors disposed within the vehicle cabin. In some implementations, the posture range 234 may include an acceptable angle or head positioning as well as body positioning. The eyelid condition range 236 may represent an acceptable range of positions of the vehicle occupant's eyelids. This may be a measurement of whether the vehicle occupant's eyes are open and alert or partially closed or closed. For example, as eyelids droop due to drowsiness or exhaustion, the eyelids may fall out of the acceptable eyelid condition range 236. In some implementations, the eyelid condition range may be monitored by the cameras 192 of the health sensor engine 140.

The pupil dilation range 238 may be indicative of an acceptable dilation for the vehicle occupant. In some implementations, the pupil dilation may be monitored by the cameras 192 of the health sensor engine 140. Abnormal pupil dilation may be indicative of a health situation. The pulse range 240, the blood pressure range 242, the stress level range 244, the body temperature range 246, and the respiration range 248 all represent acceptable physiological ranges for the vehicle occupant. In some instances, these physiological indicators may be measured by the personal sensor 155, or other sensors disposed about the cabin. In some implementations, the micro gesture camera 193 of the health sensor engine 140 may be configured to monitor and detect a pulse, blood pressure, stress level, body temperature, and or respiration of the vehicle occupant by monitoring micro gestures that are not visible to the human eye. In some implementations the health sensor engine 140 may utilize the camera 192 and the micro gesture camera 193 to identify the physiological parameters to determine whether they are within the acceptable range set forth in the health profile 230.

Figure 4:
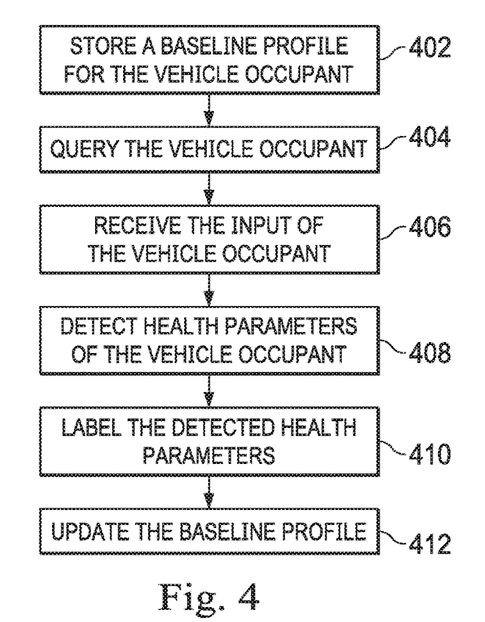
FIG. 4 is a flow diagram of a method for generating a health profile of the vehicle occupant health monitoring system according to one or more implementations of the present disclosure.

FIG. 4 is a flowchart showing a series of particular steps that may be used to create the customized health profile 230 of the profile module 210. The method may begin at 402 by storing a baseline profile for the vehicle occupant. The baseline profile may be a starting profile, or a previous profile created based on feedback or monitoring of the vehicle occupant. In some implementations, the starting profile may include a plurality of parameters measurable by the health sensor engine. The starting profile may include acceptable physiological ranges for a general population of people of any of the parameters set forth in FIG. 3. Accordingly, the initial starting profile may be based upon published health specifications that are indicative of healthy people. Alternatively, it may be a previously stored custom health profile.

At 404, the interface engine 145 may query the vehicle occupant to determine the vehicle occupant's general physiological status at a given point in time. In one example, the interface engine 145 may query the vehicle occupant each time the vehicle occupant enters or starts the vehicle 105. In one example, the interface engine 145 may utilize a voice-activated and voice recognition I/O device 202 that queries the vehicle occupant as to their health status at that moment. That is, the interface engine 145 may ask, "how are you feeling today?," for example. In other implementations, the interface engine 145 may present information seeking queries using for example a touchscreen I/O device 202, buttons, prompts, selectable faces, or other communications to receive a descriptive prompt from a vehicle occupant having a health profile.

At 406, the interface engine 145 may receive an input from the vehicle occupant. In some implementations, the input may be entered through the I/O device 202 by touching a touchscreen display, pressing a selection from a table of selectable options, or by giving a verbal response. In one example, the vehicle occupant may give a verbal response describing how they are feeling with an answer such as, for example, "good," "great," "bad," "tired," "sick," or some other verbal response. The interface engine 145 may document the vehicle occupant's response. In another example, the vehicle occupant may select one of various options from a menu to indicate his or her personal well-being. Other methods of receiving inputs indicative of the user's physical state or condition are also contemplated.

At 408, the health sensor engine 140 may detect health parameters of the vehicle occupant. For example, the health sensor engine 140 may detect the vehicle occupant's vital statistics, such as heart rate, posture, eyelid condition, pupil dilation, pulse, blood pressure, stress level, body temperature, and/or respiration, for example. This may be done using any of the sensors, including the camera 192, of the health sensor engine 140.

At 410, the vehicle control unit 110 may label the detected health parameters based upon the health-related input from the vehicle occupant at 406. For example, if the vehicle occupant was feeling tired, the vehicle control unit 110 may label the eyelid condition as a tired eyelid condition. If the vehicle occupant was feeling good, the vehicle control unit may label the eyelid condition as alert. The vehicle control unit 110 may label the any number of or all the detected health parameters forming a part of the health profile 230.

At 412, the vehicle control unit 110 may access the profile module 210 of the health monitoring engine 150, and may update the baseline health profile 230 stored therein. In some implementations, the health profile 230 may be based upon historical information obtained from the vehicle occupant. Accordingly, over time, the health profile 230 may become customized to the particular vehicle occupant, and the expected vital statistic ranges in the health profile 230 may be more accurate representations of the vehicle occupant then the public at large. This health profile 230 may be used during regular vehicle operation to identify and detect out of character or unexpected health conditions (e.g., triggering physiological conditions) represented by any of the monitored physiological conditions in the health profile 230.

The event module 212 of the health monitoring engine 150 may include an event profile that identifies one or more potential triggering events that may occur while the vehicle occupant is in the vehicle. The vehicle control unit 110 may access these triggering events and utilize the triggering events to confirm a health situation and indicate when the vehicle control unit 110 should act to mitigate potential negative outcomes resulting from the health crisis.

Figure 5:
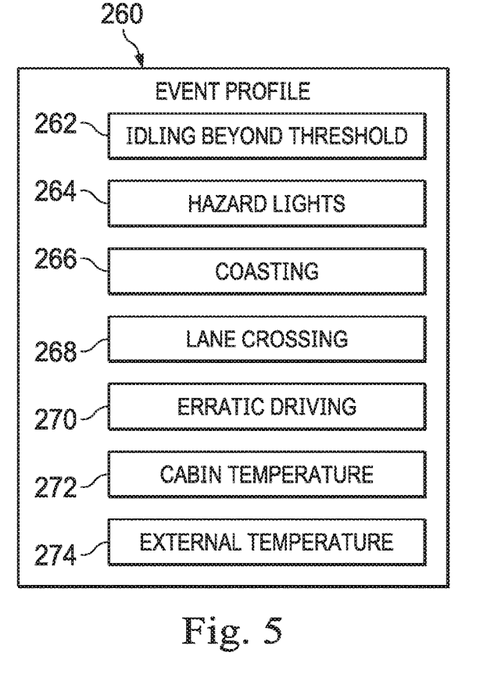
FIG. 5 is a block diagrammatic illustration of an example event profile forming a part of the vehicle occupant health monitoring system according to one or more implementations of the present disclosure

FIG. 5 discloses an event profile 260 forming a part of the event module 212 that includes a plurality of customized vehicle triggering events that may indicate to the vehicle control unit 110 that a potential health situation may be occurring. That is, the plurality of customized triggering events in the event profile 260, when combined with a physiological variance of the vehicle occupant from the health profile 230, provide some indication that a health crisis may be occurring, and the vehicle may know to automatically respond and take remedial action. In the implementation shown, the event profile 260 includes triggering events including idling beyond a pre-set time threshold 262, activation of the hazard lights 264, vehicle coasting beyond a preset distance or time threshold 266, crossing lane boundaries beyond a threshold number of times within a preestablished time period 268, erratic driving 270, excessively high or low cabin temperature 272, and/or excessively high or low external temperature 274. Other triggering events are contemplated.

In some implementations, the triggering events in the event profile 260 may be customized by the vehicle occupant and stored as a part of the event module 212. In some examples, the vehicle occupant may input the triggering events of the event profile 260 into the interface engine 145. This may be done using the I/O device 202. In some implementations, a plurality of triggering events may be presented for activation to the vehicle occupant for selection by the vehicle occupant. In some implementations, a plurality of triggering events may be displayed on the display unit 200 of the interface engine 145, and the user may select one or more of the triggering events for activation as part of the event profile 260. In other implementations, the user may enter a new desired triggering event, and the interface engine 145 may process the desired triggering event and establish a protocol for identifying when the desired triggering event occurs.

The occurrence of one or more of the triggering events identified in the event profile 260 may be detected by the vehicle operation and event sensor engine 135. For example, if the triggering event is idling for more than the preestablished time threshold, then the vehicle operation and event sensor engine 135 may monitor the engine of the vehicle 105 and the timer 184 to detect when the triggering event has occurred. For example, the event profile 260 may define a triggering event as occurring when the vehicle 105 idles for longer than 10 minutes. In another example, the event profile 260 may define a triggering event as occurring when the cabin temperature exceeds 85° F. In another example, the event profile 260 may define a triggering event as occurring when the external temperature is below 32° F. Other triggering events are contemplated herein.

The action module 214 of the health monitoring engine 150 may include an action profile that identifies one or more preestablished actions that may be taken by the vehicle control module 190 in response to the detected physiological condition of the vehicle occupant being outside the acceptable range of the health profile 230 and a triggering event set forth in the event profile 260. The preestablished actions may be actions that may minimize risk to the vehicle occupant or to others, such as pedestrians or other vehicles on the roads.

Figure 6:
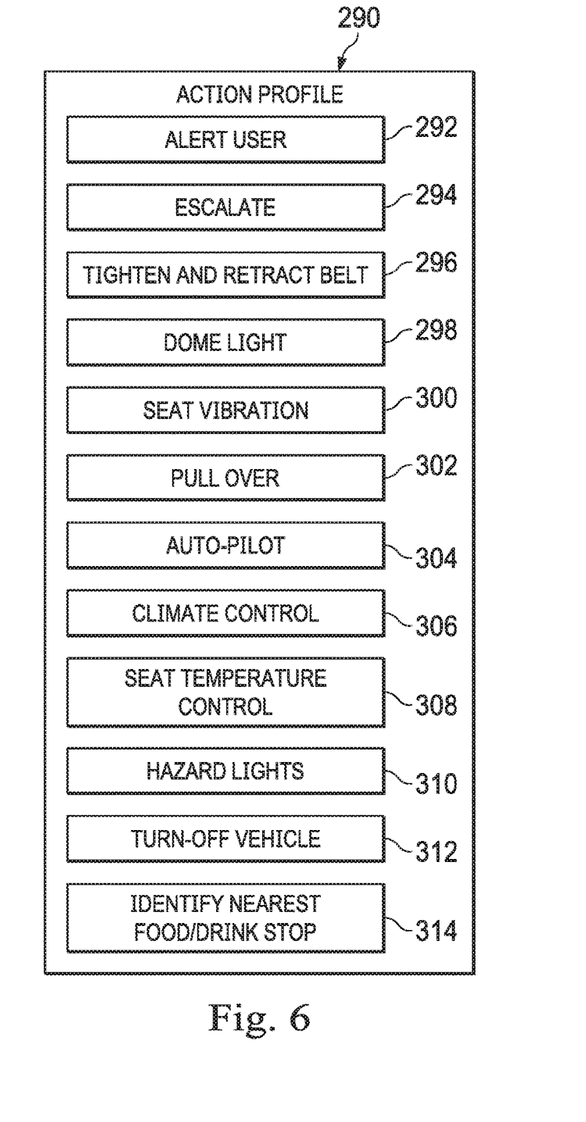
FIG. 6 is a block diagrammatic illustration of an example preestablished action profile forming a part of the vehicle occupant health monitoring system according to one or more implementations of the present disclosure

FIG. 6 identifies an action profile 290 that may be a part of the action module 214. The action profile 290 includes a plurality of customized preestablished actions or responses that the vehicle 105 may automatically take to protect the vehicle occupants and or non-occupants. In the implementation shown, the action profile 290 includes preestablished actions of alerting users 292, escalating by alerting emergency service providers 294, automatically tightening and retracting the seatbelt 296, flashing the dome light 298, vibrating the seat 300, pulling over the vehicle 105 to the side of the road 302, driving with autopilot to a preestablished destination 304, setting or adjusting the climate control to increase or decrease the cabin temperature 306, setting or adjusting seat temperature controls to increase or decrease temperatures 308, activating the hazard lights 310, turning off the vehicle 312, identifying nearest food drink stop 314, among others.

Like the event profile 260, the action profile 290 may be customized by the vehicle occupant, and it may be stored as a part of the action module 214. In some examples, the vehicle occupant may input the preestablished actions of the action profile 290 into the interface engine 145. That is, the I/O device 202 receives and stores data or information from the vehicle occupant indicative of potential actions to be automatically taken when required by the vehicle control unit 110. In some instances, actions to be taken from a list of potential actions is presented to the vehicle occupant on the display unit 200 or the I/O device 202. The vehicle occupant may then select potential actions to be taken as a result of the vehicle occupants detected physiological status being outside the health profile and the occurrence of an event in the event profile. In some implementations, certain events in the event profile 260 are associated with specific individual actions from the action profile.

The diagnosis module 216 of the health monitoring engine 150 compares the health profile 230 of the profile module 210 to the physiological parameters sensed by the health sensor engine 140 for the vehicle occupant. Accordingly, the diagnosis module 216 may communicate with the health sensor engine 140 and receive the current detected physiological vitals and statistics of the vehicle occupant. This may include any of the measurable physiological parameters identified in the health profile 230. The diagnosis module 216 may compare the detected current physiological statistics to those within the health profile 230 to determine whether any of the physiological statistics are outside an acceptable range, thereby indicating a triggering physiological condition.

Figure 7:
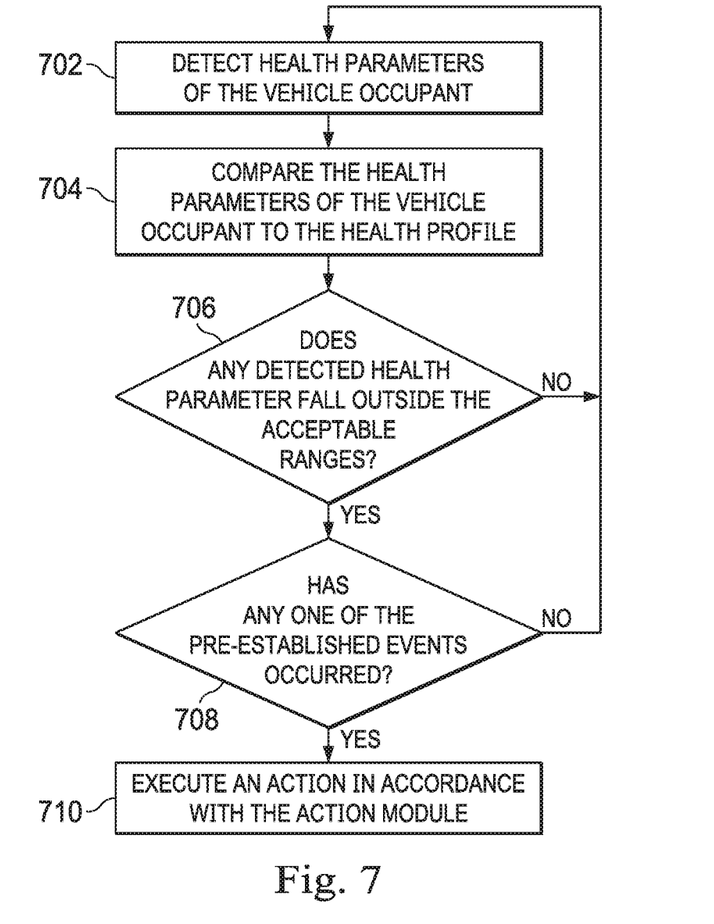
FIG. 7 is a flow diagram of a method for implementing one or more implementations of the present disclosure.

FIG. 7 is a flowchart showing an exemplary method of operating the vehicle occupant health monitoring system 100. The method begins at a step 702 of detecting an actual physiological condition of the vehicle occupant by detecting health parameters of the vehicle occupant. As indicated herein, detecting the health parameters of the vehicle occupant may include monitoring the parameters identified in the health profile of the health monitoring engine 150 with the cameras and other sensors of the health sensor engine 140. In some implementations, this may include monitoring physiological parameters such as pulse, blood pressure, stress levels, body temperature, and/or respiration utilizing cameras that capture micro gestures of the vehicle occupant. Because the micro gestures cannot be captured with the human eye, the health sensor engine 140 may be configured to recognize the micro gestures based on historical feedback for the health profile obtained over time. In some implementations, micro gesture recognition and calibration occurs based on feedback from the vehicle occupant over a period of time, including weeks or months. Because of this, the health profile in the health monitoring engine 150 may be customized and suited to the individual vehicle occupant.

At 704, the diagnosis module 216 of the health monitoring engine 150 compares the health parameters of the vehicle occupant to the stored health profile. In the implementation shown, this may include comparing the detected physiological parameters to the custom health profile to detect the presence of a triggering physiological condition. This may include identifying whether the detected physiological parameters fall outside acceptable ranges for the individual health profile. As indicated above, this may include comparing micro gestures and the resulting physiological information obtained from the micro gestures to the stored physiological information in the health profile to identify the triggering physiological condition.

At 706, the system determines whether any of the detected health parameters fall outside the acceptable physiological ranges. The acceptable physiological ranges of the health profile define boundaries or parameters of the triggering physiological conditions. If the detected health parameters are not outside the acceptable ranges stored in the health profile, then there is no triggering physiological condition and no action is taken. The method then returns to 702. However, if at 706 the detected health parameters fall outside the acceptable ranges of the health profile, then there is a triggering physiological condition and the method continues to 708. At 708, the vehicle occupant health monitoring system monitors the vehicle 105 using the vehicle operation and event sensor engine 135 to determine whether any of the preestablished events in the event module has occurred. This monitoring may take place using any of the events sensors in the vehicle operation and event sensor engine. These may include internal or external temperature sensors, lane sensors, timers, driving sensors, cameras, or other sensors such as accelerometers, speedometers, and tachometers that indicate whether an event in the event profile has occurred.

If at 708 one of the preestablished events has not occurred, then there is no triggering event and the method returns to 702 for additional monitoring. If at 708 one of the preestablished events has occurred, then there is a triggering event and the method continues to 710. At 710, the vehicle control module 190 of the vehicle operation and event sensor engine 135 controls the vehicle 105 to take an action consistent with the possible actions set forth in the action profile of the action module 214 of the health monitoring engine 150.

In some implementations, the predetermined action taken as a result of the triggering physiological condition and the triggering event is dependent upon which event is the triggering event. For example, if at 706 the triggering physiological condition is the eyelid condition, and at 708 the triggering event is coasting without pressure on the gas or brake pedals, then the action taken may include vibration of the seat to alert the driver. As another example, if at 706 the triggering physiological condition is the posture parameter, and at 708 the triggering event is erratic driving, then the action taken may include using parking assist to safely pull the vehicle over to the side of the road. Additional actions such as escalating the action over the network 130 to the emergency service providers 125 may also be taken.

In some implementations, the action profile may include alerting other occupants in the vehicle, and may also include using a notification system to alert non-occupants who may be in the vehicle occupant's contact list. The vehicle occupant health monitoring system 100 may do this using either the communication module 120 to communicate over the network 130 or may pair with the vehicle occupant's phone or other communication device to send the alert or message from the communication device.

In some implementations, the preselected action taken is dependent upon whether the detected vehicle occupant is the driver or a passenger. For example, if the detected vehicle occupant is a passenger, the vehicle control unit 110 may take a different action than if the detected vehicle occupant is the driver. For example, if the detected vehicle occupant is the driver, the vehicle control unit 110 may implement an autopilot response. However, if the detected vehicle occupant is the passenger, the vehicle control unit 110 may alert the driver to the condition of the passenger.

It is understood that variations may be made in the foregoing without departing from the scope of the present disclosure.

In some implementations, the elements and teachings of the various implementations may be combined in whole or in part in some or all the implementations. In addition, one or more of the elements and teachings of the various implementations may be omitted, at least in part, and/or combined, at least in part, with one or more of the other elements and teachings of the various implementations.

Any spatial references, such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In some implementations, while different steps, processes, and procedures are described as appearing as distinct acts, one or more of the steps, one or more of the processes, and/or one or more of the procedures may also be performed in different orders, simultaneously and/or sequentially. In some implementations, the steps, processes, and/or procedures may be merged into one or more steps, processes and/or procedures.

In some implementations, one or more of the operational steps in each implementation may be omitted. Moreover, in some instances, some features of the present disclosure may be employed without a corresponding use of the other features. Moreover, one or more of the above-described implementations and/or variations may be combined in whole or in part with any one or more of the other above-described implementations and/or variations.

Although some implementations have been described in detail above, the implementations described are illustrative only and are not limiting, and those skilled in the art will readily appreciate that many other modifications, changes and/or substitutions are possible in the implementations without materially departing from the novel teachings and advantages of the present disclosure. Accordingly, all such modifications, changes, and/or substitutions are intended to be included within the scope of this disclosure as defined in the following claims.

What is claimed is:

1. A vehicle occupant health monitor system, comprising:
an interface engine including a processor configured to receive inputs from a vehicle occupant defining a triggering event, a triggering physiological condition, and a preestablished action, wherein the triggering event comprises a condition of a vehicle;
a health profile module comprising a custom health profile for the vehicle occupant defining a parameter of the triggering physiological condition;
a sensor arranged to monitor an actual physiological condition of the vehicle occupant for the triggering physiological condition;
a diagnosis module including a processor configured to compare the actual physiological condition of the vehicle occupant to the custom health profile to detect a presence of the triggering physiological condition; and
a vehicle control module including a processor configured to:
detect a presence of the triggering event;
confirm a presence of the triggering physiological condition based on detecting the presence of the triggering event; and
perform the preestablished action when both a) the processor of the diagnosis module detects the presence of the triggering physiological condition and b) the processor of the vehicle control module detects the condition of the vehicle.

2. The system of claim 1, wherein the custom health profile comprises at least one of an expected heart rate range, an expected posture range, an accepted pulse range, an accepted blood pressure range, an accepted stress level range, an expected body temperature range, or an expected respiration range.

3. The system of claim 2, further comprising a user interface configured to receive an input from the vehicle occupant regarding a current physiological condition of the vehicle occupant, and configured to update the custom health profile based on the received input.

4. The system of claim 3, wherein the user interface is configured to query the vehicle occupant regarding the current physiological condition of the vehicle occupant.

5. The system of claim 1, comprising an action module comprising the preestablished action, the preestablished action being based upon an input from the vehicle occupant.

6. The system of claim 5, further comprising a user interface configured to receive an input from the vehicle occupant, the user interface being configured to present a plurality of potential preestablished actions to the vehicle occupant, and configured to receive via the user interface a selected preestablished action.

7. The system of claim 1, comprising an event module comprising the triggering event, the triggering event being based upon an input from the vehicle occupant.

8. The system of claim 7, further comprising a user interface configured to present a plurality of potential triggering events to the vehicle occupant, and configured to receive a selected triggering event.

9. The system of claim 1, comprising an event module comprising a plurality of triggering events, the triggering events comprising at least one of hazard lights being activated, the vehicle being at an erratic driving condition, or the vehicle being idled beyond a set period of time.

10. The system of claim 1, wherein the sensor is a micro gesture detecting camera configured to detect one of a pulse, a blood pressure, a stress level, a body temperature, or respiration of the vehicle occupant.

11. The system of claim 1, wherein the custom health profile defines a parameter of the triggering physiological condition by defining an expected physiological condition.

12. A vehicle occupant health monitor system, comprising:
a sensor arranged within a vehicle to monitor a sensed physiological condition of a vehicle occupant while in the vehicle;
a profile module comprising a vehicle occupant health profile that comprises at least one expected physiological condition, the profile module including a processor;
a diagnosis module including a processor configured to compare the sensed physiological condition of the vehicle occupant to the expected physiological condition of the health profile and identify a presence of a triggering physiological condition, the processor of the profile module configured to update the health profile based on the sensed physiological condition;
an interface engine including a processor configured to receive an input from the vehicle occupant defining a triggering event, a triggering physiological condition, and a preestablished action, the triggering event comprising a condition of the vehicle; and
a vehicle control module including a processor arranged to:
detect a presence of the triggering event,
confirm a presence of the triggering physiological condition based on detecting the presence of the triggering event; and
perform the preestablished action after the processor of the profile module updates the health profile and when both a) the processor of the diagnosis module identifies the presence of the triggering physiological condition and b) the processor of the vehicle control module detects the condition of the vehicle.

13. The system of claim 12, comprising:
a user interface configured to receive information from the vehicle occupant regarding a physiological condition of the vehicle occupant, and
wherein the processor of the profile module is configured to update the health profile based on the information from the vehicle occupant regarding the physiological condition of the vehicle occupant.

14. The system of claim 13, wherein the user interface is configured to query the vehicle occupant regarding the physiological condition of the vehicle occupant.

15. The system of claim 12, wherein the sensor is a micro gesture detecting camera configured to detect one of a pulse, a blood pressure, a stress level, a body temperature, or respiration of the vehicle occupant.

16. The system of claim 12, wherein the health profile comprises at least one of an expected heart rate range, an expected posture range, an accepted pulse range, an accepted blood pressure range, an expected stress level range, an expected body temperature range, or an expected respiration range.

17. A method of monitoring and responding to a vehicle occupant's health, comprising:
  generating a custom health profile for a vehicle occupant comprising at least one expected physiological condition;
  receiving an input with a processor of an interface engine from the vehicle occupant defining a triggering event, a triggering physiological condition, and a preestablished action, the triggering event comprising a condition of a vehicle;
  monitoring with a sensor an actual physiological condition of the vehicle occupant;
  comparing with a processor of a diagnosis module the actual physiological condition of the vehicle occupant to the expected physiological condition to identify a presence of the triggering physiological condition;
  detecting with a processor of a vehicle control module a presence of the triggering event;
  confirming with the processor of the vehicle control module the presence of the triggering physiological condition based on detecting the presence of the triggering event; and
  performing with the processor of the vehicle control module the preestablished action when both a) the processor of the diagnosis module detects a presence of the expected physiological condition and b) the processor of the vehicle control module detects the condition of the vehicle.

18. The method of claim 17, wherein monitoring with the sensor comprises monitoring with a micro gesture detecting camera configured to detect one of a pulse, a blood pressure, a stress level, a body temperature, or respiration of the vehicle occupant.

19. The method of claim 17, comprising:
  receiving at an input device information from the vehicle occupant regarding a current physiological condition of the vehicle occupant, and
  updating the custom health profile based on the information from the vehicle occupant regarding the current physiological condition of the vehicle occupant.

20. The method of claim 19, comprising querying the vehicle occupant regarding the current physiological condition of the vehicle occupant.

* * * * *